United States Patent [19]

Flesch et al.

[11] Patent Number: 5,296,475
[45] Date of Patent: Mar. 22, 1994

[54] PHARMACEUTICAL COMPOSITIONS COMPRISING METHANEDIPHOSPHONIC ACID DERIVATIVES AND MACROCYCLIC POLYETHERS

[75] Inventors: Gérard Flesch, Mulhouse; Jean-Marie Lehn, Strasbourg, both of France

[73] Assignee: Ciba-Geigy Corporation, Ardsley, N.Y.

[21] Appl. No.: 992,206

[22] Filed: Dec. 17, 1992

[30] Foreign Application Priority Data

Dec. 19, 1991 [CH] Switzerland ............. 3779/91
Jan. 27, 1992 [CH] Switzerland ............. 215/92

[51] Int. Cl.$^5$ ........................... A61K 31/66
[52] U.S. Cl. .................. 514/108; 514/784; 514/788; 514/946
[58] Field of Search ............. 514/108, 450, 784, 788, 514/946

[56] References Cited

U.S. PATENT DOCUMENTS

| | | |
|---|---|---|
| 3,962,432 | 6/1976 | Schmidt-Dünker . |
| 4,134,969 | 1/1979 | Schmidt-Dünker . |
| 4,269,828 | 5/1981 | Flora et al. ............. 424/204 |
| 4,275,059 | 6/1981 | Flora et al. ............. 424/204 |
| 4,980,171 | 12/1990 | Fels et al. ............. 424/473 |
| 5,096,717 | 3/1992 | Wirth et al. ............. 424/490 |

FOREIGN PATENT DOCUMENTS

| | | | |
|---|---|---|---|
| 0088462 | 9/1983 | European Pat. Off. ...... A61K 45/06 |
| 0341409 | 11/1989 | European Pat. Off. ...... C07F 15/00 |
| 0381296 | 8/1990 | European Pat. Off. ...... A61K 31/66 |
| 2405254 | 8/1975 | Fed. Rep. of Germany . |

OTHER PUBLICATIONS

Derwent Abstract 89-249746/35 Corresponding to PCT 89/7453, 1989.
Dutton et al. "Synthesis and Metal Ion Complexation Behavior of Polycarboxylate 18-Crown-6 Ethers Derived from Tartaric Acid", Can. J. Chem. 66, pp. 1097–1108 (1988).
Hrigiga et al. "pH Regulation of Divalent/Monovalent Ca/K Cation Transport Selectivity by a Macrocyclic Carrier Molecule", Proc. Natl. Acad. Sci. USA, 80, pp. 6426–6428 (1983).
European Patent Office Search Report, May 18, 1993 for EP 92 81 0990.
Helvetica Chimica Acta, 65, pp. 1853–1867, 1982.
Helvetica Chimica Acta, 63, pp. 2096–2111, 1980.
Behr et al. 220. "Molecular Receptors. Functionalized and Chiral Macrocyclic Polyethers Derived from Tartaric Acid".
Journal of Chromatography, 489, pp. 446–451, 1989. Flesch et al.
Journal of Chromatography, 568, pp. 261–266, 1991. Flesch et al.

*Primary Examiner*—S. J. Friedman
*Assistant Examiner*—William Jarvis
*Attorney, Agent, or Firm*—Irving M. Fishman; Karen G. Kaiser; Barbara J. Ikeler

[57] ABSTRACT

The invention relates to pharmaceutical compositions for peroral administration comprising (a) pharmaceutically useful methanediphosphonic acid derivatives, e.g. those of formula I

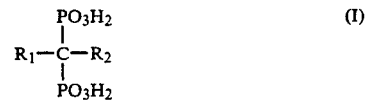

wherein $R_1$ and $R_2$ are as defined in the specification, or pharmaceutically acceptable salts thereof, (b) specific macrocyclic polyethers and optionally (c) pharmaceutically acceptable adjuvants. The pharmaceutical compositions are prepared in a manner known per se. A method of treating hypercalcemia and osteolytic bone metastases with these compositions is also disclosed herein.

15 Claims, No Drawings

PHARMACEUTICAL COMPOSITIONS COMPRISING METHANEDIPHOSPHONIC ACID DERIVATIVES AND MACROCYCLIC POLYETHERS

Methanediphosphonic acid derivatives are commonly used, inter alia, for the treatment of osteolytic bone metastases and hypercalcaemia, as they are able to inhibit the growth and the decomposition of hydroxy apatite. These compounds inhibit bone resorption by spontaneous binding to the hydroxyapatite of the bone, so that osteoclases are no longer able to split off hydroxyapatite crystals. Compounds of this class are disclosed, inter alia, in DE-OS 2 405 254.

It is known that methanediphosphonic acid derivatives, after peroral administration, are only resorbed to an insignificant degree in the gastro-intestinal tract. They therefore have to be administered perorally in higher dosage or parentally in order to achieve the desired therapeutic effect.

Because of the importance of this class of compounds for the treatment of osteoporosis, Paget's disease, Bechterew's disease as well as the formation of bone metastases, many efforts are being directed to the provision of a pharmaceutical dosage form for peroral administration in which the active drugs are resorbed to a greater degree.

Surprisingly, it has now been found that methanediphosphonic acid derivatives are substantially better resorbed after peroral administration if they are administered together with specific macrocyclic polyethers.

Accordingly, it is the object of this invention to provide pharmaceutical compositions for peroral administration comprising
(1) at least one pharmaceutically useful methanediphosphonic acid derivative,
(2) at least one macrocyclic polyether of formula II

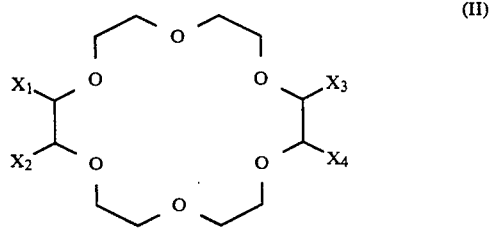

(II)

wherein $X_1$–$X_4$ are each independently of the other carboxy, carbamoyl or N-mono- or N,N-disubstituted carbamoyl, or a pharmaceutically acceptable salt thereof, and optionally (3) pharmaceutically acceptable adjuvants.

A pharmaceutically useful methanediphosphonic acid derivative has, for example, the structure of formula I

(I)

wherein $R_1$ is hydrogen, hydroxy, amino or halogen, and $R_2$ is halogen or a radical which is bound through C, N, S or O, and also embraces corresponding pharmaceutically acceptable salts.

Preferred pharmaceutical compositions comprise as methanedisphosphonic acid derivative at least one compound of formula I, wherein (a) $R_1$ and $R_2$ are each independently of the other halogen or (b) $R_1$ is hydrogen and $R_2$ is a group Ar—S—, Het$_1$—NH—, Cyc—NH—, Ar—S—A—N(R')— or Het$_3$—S—A—N(R')—, wherein Ar is unsubstituted or substituted phenyl, Het$_1$ and Het$_3$ are each unsubstituted or substituted monocyclic 5- or 6-membered monoaza-, diaza- or thiaza-aryl which is bound through a ring carbon atom, Cyc is cycloalkyl, A is alkylene and R' is hydrogen or lower alkyl, or (c) $R_1$ is hydrogen or hydroxy and $R_2$ is —A—$R_3$, wherein A is alkylene, and
$R_3$ is either Het$_2$, which has the meaning of Het$_1$ but can be bound through a ring carbon atom or a ring nitrogen atom, or
$R_3$ is hydrogen or unsubstituted amino or amino which is mono- or disubstituted by alkyl, cycloalkyl, Ar-alkyl, Ar-O-alkyl, Ar-S-alkyl or Het$_1$-alkyl each independently of one another, and Ar and Het$_1$ are as defined above, or
$R_3$ is unsubstituted or Ar-substituted alkyleneamino, wherein two alkylene carbon atoms may be additionally linked to each other through alkylene, and Ar is as defined above,
or a pharmaceutically acceptable salt thereof.

Salts of compounds of formula I are preferably salts thereof with bases, conveniently metal salts derived from groups Ia, Ib, IIa and IIb of the Periodic Table of the Elements, including alkali metal salts, preferably sodium or potassium salts, alkaline earth metal salts, preferably calcium or magnesium salts, and also ammonium salts with ammonia or organic amines.

Substituted phenyl is mono- or polysubstituted, for example di- or trisubstituted, e.g. by lower alkyl, lower alkoxy, trifluoromethyl and/or preferably halogen.

Monocyclic 5- or 6-membered monoaza-aryl, diaza-aryl or thiaza-aryl is e.g. pyrrolyl, imidazolyl, including 1-, 2-, 4- or 5-imidazolyl, pyrazolyl such as 1- or 3-pyrazolyl, thiazolyl such as 2- or 4-thiazolyl, pyridyl such as 2-, 3- or 4-pyridyl. Corresponding radicals can be substituted by one or more than one, e.g. by two or three, of e.g. alkyl group(s). Preferred substituted radicals include alkyl-substituted 1-imidazolyl and 5-imidazolyl, 5-lower alkyl-2-thiazolyl such as 5-methyl-2-thiazolyl, 5-ethyl-2-thiazolyl and 5-n-butyl-2-thiazolyl, as well as alkyl-substituted 2- and 3-pyridyl.

Unsubstituted or substituted monocyclic 5- or 6-membered monoaza-aryl, diaza-aryl or thiaza-aryl which is bound through a ring carbon atoms is preferably a radical selected from the group consisting of 2-, 4- or 5-imidazolyl, 3-pyrazolyl, thiazolyl, e.g. 2- or 4-thiazolyl, and pyridyl, e.g. 2-, 3- or 4-pyridyl, and which is unsubstituted or substituted by lower alkyl.

Unsubstituted or substituted monocyclic 5- or 6-membered monoaza-aryl, diaza-aryl or thiaza-aryl which is bound through a ring carbon atom or a ring nitrogen atom is preferably a radical selected from the group consisting of pyrrolyl, imidazolyl, pyrazolyl, thiazolyl or pyridyl which is unsubstituted or substituted by lower alkyl.

Alkyl is preferably lower alkyl, alkylene is preferably lower alkylene, and Ar-alkyl is e.g. phenyl-lower alkyl which may be substituted in the phenyl nucleus as indicated above.

Cycloalkyl is preferably $C_3$–$C_7$cycloalkyl, e.g. cyclopropyl, cyclobutyl, cyclopentyl, cyclohexyl or cycloheptyl.

Amino which is mono- or disubstituted by alkyl, cycloalkyl, Ar-alkyl, Ar-O-alkyl, Ar-S-alkyl or $Het_1$-alkyl is preferably lower alkylamino, $C_3$–$C_7$cycloalkylamino, phenyl-lower alkylamino, di-lower alkylamino, lower alkyl-phenyl-lower alkylamino, diphenyl-lower alkylamino, phenoxy-lower alkylamino, lower alkylphenoxy-lower alkylamino, phenoxy-lower alkylphenyl-lower alkylamino, diphenoxy-lower alkylamino, phenylthio-lower alkylamino, lower alkylphenylthio-lower alkylamino, phenylthio-lower alkylaminophenyl-lower alkylamino, diphenylthio-lower alkylamino, lower alkylpyridyl-lower alkylamino, phenyl-lower alkylpyridyl-lower alkylamino, phenoxy-lower alkylpyridyl-lower alkylamino, phenylthio-lower alkylpyridyl-lower alkylamino or dipyridyl-lower alkylamino, the phenyl or pyridyl moiety of which radicals may be substituted as indicated above.

Unsubstituted or Ar-substituted alkyleneamino is preferably lower alkyleneamino, e.g. 1,4-butyleneamino (=pyrrolidin-1-yl) or 1,5-pentyleneamino (=piperidin-1-yl), or lower alkyleneamino which is substituted by a phenyl radical which is unsubstituted or substituted as indicated above, e.g. 2-(4-chlorophenyl)-1,4-butyleneamino or 3-phenyl-1,5-pentyleneamino.

Alkyleneamino in which two alkylene carbon atoms are additionally linked to each other through alkylene is preferably lower alkyleneamino wherein two, preferably non-adjacent, lower alkylene carbon atoms are linked to each other through lower alkylene, in particular methylene. Corresponding 3-azabicyclo-$C_6$–$C_{10}$alk-3-yl radicals are preferred.

The general definitions cited above have the following preferred meanings, unless otherwise defined.

Halogen is preferably halogen having an atomic number of up to 35 inclusive, e.g. fluoro or bromo, and also iodo, preferably chloro.

Lower alkyl is e.g. methyl, ethyl, n-propyl, isopropyl, n-butyl, isobutyl, sec- and tert-butyl, and in addition embraces corresponding pentyl, hexyl and heptyl radicals. $C_1$–$C_4$Alkyl is preferred.

Lower alkoxy is e.g. methoxy, ethoxy, n-propoxy, isopropoxy and n-butoxy and in addition embraces corresponding pentoxy, hexoxy and heptoxy radials. $C_1$–$C_4$Alkoxy is preferred.

Lower alkylene is straight-chain or branched and is e.g. $C_1$–$C_7$alkylene such as methylene, ethylene, propylene, butylene, pentyiene, and also hexylene and heptylene, as well as 2-methyl-1,3-propylene, 2,4- or 1,5-dimethyl-1,5-pentylene. Lower alkylene as substituent of disubstituted amino $R_3$ contains at least two carbon atoms, preferably 4 to 6 carbon atoms. Lower alkylene which links together two lower alkylene carbon atoms of amino which is disubstituted by lower alkylene contains preferably up to 5 carbon atoms inclusive is preferably methylene.

$C_1$–$C_3$Alkyl is methyl, ethyl, n-propyl and isopropyl.

Carbamoyl is the group —$CONH_2$.

N-mono-substituted carbamoyl is e.g. N-lower alkylcarbamoyl, N-(amino-lower alkyl)carbamoyl; N-arylcarbamoyl, wherein aryl is phenyl or naphthyl which are each unsubstituted or substituted by carboxy and/or —$SO_3H$; N-[(lower alkoxycarbonyl or carboxy)-lower alkyl]carbamoyl or N-[(3-carbamoyl-1-pyridinium)-lower alkyl]carbamoyl.

N,N-Disubstituted carbamoyl is e.g. N,N-di-lower alkylcarbamoyl.

N-Mono- and N,N-disubstituted carbamoyl further encompasses those radicals in which the amidic nitrogen atom is formed by an alpha-amino acid and is therefore suitably monosubstituted (or e.g. in the case of proline disubstituted). The carbamoyl radicals derived from glycine, proline, phenylalanine, tryptophane, glutaminic acid and arginine are of particular interest. In these the carboxy groups of the respective amino acid may be in the free form, in salt form or also derivatised form, e.g. as lower alkyl esters or carboxamides.

Radicals or compounds qualified by the term "lower" contain up to 7 carbon atoms inclusive, preferably up to 4 carbon atoms inclusive.

In preferred macrocyclic polyethers of formula II the substituents $X_1$–$X_4$ are identical.

Particularly preferred macrocyclic polyethers of formula II are those of formula IIa

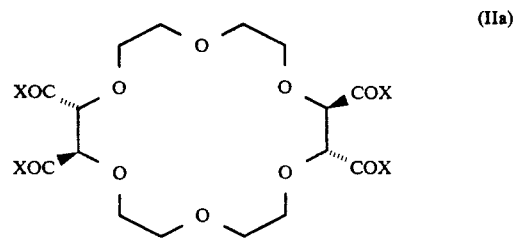

(IIa)

wherein the substituents X are identical and are hydroxy, as well as pharmaceutically acceptable salts thereof. These polyethers are (+)-1,4,7,10,13,16-hexaoxa-cyclooctadecane-2,3,11,12-tetracarboxylic acid [abbreviated to: (+)-18-crown-6-tetracarboxylic acid] and pharmaceutically useful salts thereof. The free (+)-1,4,7,10,13,16-hexaoxa-cyclooctadecane-2,3,11,12-tetracarboxylic acid is especially preferred.

In the pharmaceutical compositions of this invention the components (1) [=pharmaceutically useful methanediphosphonic acid derivative or derivatives)] and (2) [=macrocyclic polyether or polyethers] are preferably in the ratio of 1:1 to 1:16, more particularly 1:1 to 1:8 and, most preferably, 1:2 to 1:6.

The pharmaceutically useful methanediphosphonic acid derivatives are known or can be prepared in a manner known per se.

Thus, for example, compounds of formula I, wherein $R_1$ is hydrogen and $R_2$ is Ar—S—, are obtainable by reacting tetra-lower alkyl methanediphosphonate in the presence of a strong metal base such as NaH, with a disulfide of formula Ar—S—S—Ar and subsequent acid hydrolysis of the tetra-lower alkyl ester (q.v. inter alia EP-A-100 718).

Corresponding compounds of formula I, wherein $R_1$ is hydrogen and $R_2$ is $Het_1$—NH—, may be e.g. prepared by reacting a mixture of $H_3PO_3$ and $PHal_3$, wherein Hal is halogen, preferably chloro, with a formylamine of formula $Het_1$—NH—CHO, or by heating an amine $Het_1$—$NH_2$ with a lower alkyl orthoformate and a di-lower alkyl phosphite and hydrolysing the reaction product, conveniently in the presence of an acid (q.v. inter alia EP-A-274 346).

Compounds of formula I, wherein $R_1$ is hydrogen and $R_2$ is —A—$R_3$, and A is alkylene, may be prepared by starting from compounds of formula $R_3$—A—Hal and reacting these with a tetra-lower alkyl methanediphosphonate in the presence of a strong base, e.g. NaH, and hydrolysing the resultant tetra-lower alkyl esters of corresponding compounds of formula I, conveniently in the presence of an acid such as hydrochloric acid (q.v. inter alia EP-A-275 821).

Compounds of formula I, wherein $R_1$ is hydroxy and $R_2$ is $-A-R_3$, may e.g. be prepared by reacting a carboxylic acid of formula $R_2-COOH$ with a phosphorylating agent, as with a mixture of $H_3PO_3$ and $PHal_3$, and working up the reaction product under hydrolytic conditions (q.v. inter alia EP-A-170 228 and EP-A-252 505).

The preparation of compounds of formula Ia (q.v. below) and pharmaceutically acceptable salts thereof is disclosed, inter alia, in DE-OS-2 405 254.

The preparation of the macrocyclic polyethers of formula II is described, inter alia, by J.-P. Behr et al., Helv. Chim. Acta 65, 1853–1867 (1982) or J.-P. Behr et al., Helv. Chim. Acta 63, 2096–2111 (1980). A compound of formula II, wherein $X_1=X_2=X_3=X_4=CON(CH_3)_2$, may be prepared by reacting N,N,N',N'-tetramethyltartramide first with thallium(I) ethoxide and then with 1,5-diiodo-3-oxapentane. The compound so obtained can be converted e.g. by acid hydrolysis, conveniently with hydrochloric acid, into another compound of formula II, wherein $X_1$, $X_2$, $X_3$ and $X_4$ are carboxy.

The pharmaceutically useful methanediphosphonic acid derivatives have valuable pharmacological properties. In particular they exert a pronounced regulatory action on the calcium metabolism of warm-blooded animals. They also induce a marked inhibition of bone resorption in rats, as can be shown both in the assay described in Acta Endocrinol. 78, 613–24 (1975) as well as in the TPTX (thyroparathyroid ectomised) rat model by means of vitamin $D_3$ induced experimental hypercalcaemia. The tumour hypercalcaemia induced by Walker-256-tumours is likewise inhibited after peroral administration. Further, when used for the treatment of adjuvant arthritis in rats in the assay of Newbould, Brit. J. Pharmacology 21, 127 (1963) and of Kaibara et al., J. Exp. Med. 159, 1388–96 (1984) they exhibit a marked inhibition of the progression of chronic arthritic processes. They are therefore pre-eminently suitable for use as the active principle of medicaments for the treatment of diseases that can be attributed to disorders of calcium metabolism, typically inflammatory processes in joints, degenerative processes in articular cartilage, for the treatment of osteoporosis, periodontitis, hyperparathyroidism and of calcium deposits in blood vessels or prothetic implants. They also have a beneficial effect on diseases in which an abnormal deposit of poorly soluble calcium salts is observed, as in arthritic diseases such as Bechterew's disease, neuritis, bursitis, periodontitis and tendinitis, fibrodysplasia, osteoarthritis or artereosclerosis, as well as in diseases in which an anomalous disintegration of hard body tissue is a prime feature, typically hereditary hypophosphatasia, degenerative processes in articular cartilage, osteoporoses of different provenance, Paget's disease and osteodystrophia fibrosa, and also osteolytic processes induced by tumours as well as hypercalcaemia. Individual representatives of the class of compounds defined above are already in therapeutic use.

The gastro-intestinal absorption of the active drug can, for example, be determined from the secretion of the active drug in urine over a period of 0–96 hours after a single peroral administration of the novel pharmaceutical composition to e.g. dogs. It is found that the resorbed dose of active drug on administration of the inventive pharmaceutical composition is increased by a factor of about 10 or more in comparison with administration of the drug in the form of e.g. an enteric-coated tablet or of enteric-coated pellets.

The invention relates in particular to pharmaceutical compositions comprising at least one pharmaceutically useful methanediphosphonic acid derivative of formula I, wherein (a) $R_1$ and $R_2$ are each independently of the other halogen, or (b) $R_1$ is hydrogen and $R_2$ is a group Ar—S—, $Het_1$—NH—, Cyc—NH—, Ar—S—A—NH— or $Het_3$—S—A—NH—, wherein Ar is unsubstituted phenyl or phenyl which is substituted by lower alkyl, lower alkoxy, trifluoromethyl and/or halogen, $Het_1$ is unsubstituted thiazolyl or thiazolyl which is substituted by lower alkyl, Cyc is $C_3$–$C_7$cycloalkyl, A is lower alkylene and $Het_3$ is thiazolyl or pyridyl, which are each unsubstituted or substituted by lower alkyl, or (c) $R_1$ is hydrogen or hydroxy and $R_2$ is $-A-R_3$, wherein A is lower alkylene, and $R_3$ is either unsubstituted or lower alkyl-substituted imidazolyl which is bound through a ring carbon atom or a ring nitrogen atom, or is pyridyl, or $R_3$ is hydrogen or unsubstituted amino or amino which is mono- or disubstituted by lower alkyl, $C_3$–$C_7$cycloalkyl, Ar-lower alkyl, Ar—O-lower alkyl, Ar—S-lower alkyl or pyridyl-lower alkyl, each independently of one another, and Ar is as defined above, or $R_3$ is unsubstituted or Ar-substituted $C_4$–$C_6$alkyleneamino, wherein two non-adjacent lower alkylene carbon atoms may be additionally linked to each other through $C_1$–$C_3$alkylene, and Ar is as defined above, or a pharmaceutically acceptable salt thereof.

The invention relates more particularly to pharmaceutical compositions comprising a pharmaceutically useful methanediphosphonic acid of formula I, wherein (a) $R_1$ and $R_2$ are halogen, or (b) $R_1$ is hydrogen and $R_2$ is unsubstituted or halogen-substituted phenylthio, unsubstituted or lower alkyl-substituted thiazolylamino or $C_5$–$C_7$cycloalkylamino, or (c) $R_1$ is hydrogen or hydroxy and $R_2$ is $-A-R_3$, wherein A is $C_1$–$C_7$alkylene and $R_3$ is an unsubstituted or lower alkyl-substituted imidazolyl radical which is bound through a ring carbon atom or a ring nitrogen atom, or is pyridyl, or (d) $R_1$ is hydroxy and $R_2$ is $-A-R_3$, wherein A is $C_1$–$C_7$alkylene und $R_3$ is amino, di-$C_1$–$C_5$alkylamino, N-$C_3$–$C_7$cycloalkylamino, N-$C_1$–$C_4$alkyl-N-phenyl-$C_1$–$C_5$alkylamino, N-$C_1$–$C_4$alkyl-N-phenoxy-$C_1$–$C_4$alkyl, N-$C_1$–$C_4$alkyl-N-phenylthio-$C_1$–$C_4$alkyl, N-$C_1$–$C_4$alkyl-N-pyridyl-$C_1$–$C_4$alkylamino; $C_4$–$C_6$alkyleneamino which is unsubstituted or substituted by phenyl which is in turn unsubstituted or substituted by halogen; or 1,5-di-$C_1$–$C_4$alkyl-3-aza-bicyclo[3.1.1]hept-3-yl, or (e) $R_1$ is hydroxy and $R_2$ is $-A-R_3$, wherein A is $C_1$–$C_4$alkylene, and $R_3$ is hydrogen, or a pharmaceutically acceptable salt thereof.

The invention relates preferably to pharmaceutical compositions comprising a pharmaceutically useful methanediphosphonic acid of formula I, wherein (a) $R_1$ and $R_2$ are chloro, or (b) $R_1$ is hydrogen and $R_2$ is unsubstituted or chlorosubstituted phenylthio, unsubstituted or $C_1$–$C_4$alkyl-substituted thiazolylamino, or is cycloheptylamino, or (c) $R_1$ is hydrogen or hydroxy and $R_2$ is —A—$R_3$, wherein A is methylene, ethylene, propylene or pentylene, and $R_3$ is imidazol-1-yl, imidazol-5-yl, 1-methylimidazol-2-yl, 4-methylimidazol-5-yl, or 2- or 3-pyridyl, or (d) $R_1$ is hydroxy and $R_2$ is —A—$R_3$, wherein A is methylene, ethylene, propylene or pentylene, and $R_3$ is amino, dimethylamino, N-methyl-N-n-propylamino, N-methyl-N-n-pentylamino, N-cycloheptylamino, N-methyl-N-(2-phenylethyl)amino, N-methyl-N-(3-phenylpropyl)amino or N-methyl-N-(5-phenylpentyl)amino, N-methyl-N-(3-phenoxypropyl)amino, N-methyl-N-(2-phenylthioethyl)amino, N-methyl-N-(3-phenylthiopropyl)amino, N-methyl-N-[3-(2-pyridyl)propyl]amino, piperidin-1-yl, which is unsubsituted or substituted in 4-position by phenyl, or pyrrolidin-1-yl, which is unsubstituted or substituted in 3-position by 4-chlorophenyl, or is 1,5-dimethyl-3-azabicyclo[3.1.1]hept-3-yl, or (e) $R_1$ is hydroxy and $R_2$ is —A—$R_3$, wherein A is methylene and $R_3$ is hydrogen, or a pharmaceutically acceptable salt thereof.

The invention relates very particularly to pharmaceutical compositions which comprise a pharmaceutically active methanediphosphonic acid selected from the following group of compounds of formula I:

4-amino-1-hydroxybutane-1,1-diphosphonic acid, 6-amino-1-hydroxyhexane-1,1-diphosphonic acid, 3-(N-methyl-N-n-pentylamino)-1-hydroxypropane-1,1-diphosphonic acid, 3-[N-(3-phenylpropyl)-N-methylamino]-1-hydroxypropane-1,1-diphosphonic acid, 3-(N-methyl-N-5-phenylpentylamino)-1-hydroxypropane-1,1-diphosphonic acid, 3-[N-methyl-N-3-(2-pyridyl)propylamino]-1-hydroxypropane-1,1-diphosphonic acid, 1-hydroxy-3-[N-methyl-N-(3-phenoxypropyl)amino]propane-1,1-diphosphonic acid, 1-hydroxy-3-[N-methyl-N-(2-phenoxyethyl)amino]propane-1,1-diphosphonic acid, 4-(4-phenylpiperidin-1-yl)-1-hydroxybutane-1,1-diphosphonic acid, 1-hydroxy-3-(1-piperidino)propane-1,1-diphosphonic acid, 1-hydroxy-3-[3-(4-chlorophenyl)pyrrolidin-1-yl]propane-1,1-diphosphonic acid, 1-hydroxy-2-(imidazol-1-yl)ethane-1,1-diphosphonic acid, 2-(1-methylimidazol-2-yl)ethane-1,1-diphosphonic acid, 1-hydroxy-2-(4-methylimidazol-5-yl)ethane-1,1-diphosphonic acid, 1-hydroxy-2-(imidazol-5-yl)ethane-1,1-diphosphonic acid, 1-hydroxy-2-(3-pyridyl)ethane-1,1-diphosphonic acid, 2-(2-pyridyl)ethane-1,1-diphosphonic acid, 1-[(5-n-butyl-2-thiazolyl)amino]methane-1,1-diphosphonic acid, 1-[(5-methyl-2-thiazolyl)amino]methane-1,1-diphosphonic acid, 1-[(2-thiazolyl)amino]-methane-1,1-diphosphonic acid, 1-hydroxyethane-1,1-diphosphonic acid, 1-(4-chlorophenylthio)methane-1,1-diphosphonic acid, 1,1-dichloromethane-1,1-diphosphonic acid, 3-(1,5-dimethyl-3-azabicyclo[3.1.1]hept-3-yl)-1-hydroxypropane-1,1-diphosphonic acid, 1-[(5-ethyl-2-thiazolyl)amino]methane-1,1-diphosphonic acid, 3-[N-(2-phenylethyl)-N-methyl-amino]1-hydroxypropane-1,1-diphosphonic acid, 3-[N-(2-phenylthioethyl)-N-methylamino]1-hydroxypropane-1,1-diphosphonic acid, 3-[N-(3-phenylthiopropyl)-N-methylamino]1-hydroxypropane-1,1-diphosphonic acid, 1-hydroxy-3-(pyrrolidin-1-yl)propane-1,1-diphosphonic acid, 2-(N-cyclohexylamino)ethane-1,1-diphosphonic acid, 1-(N-cycloheptylamino)methane-1,1-diphosphonic acid, 2-(N,N-dimethylamino)-1-hydroxyethane-1,1-diphosphonic acid, 3-amino-1-hydroxypropane-1,1-diphosphonic acid, 3-(N,N-dimethylamino)-1-hydroxypropane-1,1-diphosphonic acid, 3-(N-methyl-N-n-propylamino)-1-hydroxypropane-1,1-diphosphonic acid, 1-[N-(4-phenylthiobutyl)amino]methane-1,1-diphosphonic acid, 1-{N-[4-(2-pyridyl)thiobutyl]amino}methane-1,1-diphosphonic acid, or a pharmaceutically acceptable salt thereof.

The invention relates especially to the pharmaceutical compositions comprising as pharmaceutically active methanediphosphonic acid derivative a compound of formula Ia

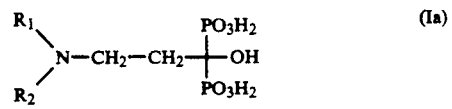

wherein $R_1$ and $R_2$ are each independently of the other hydrogen or $C_1$–$C_3$alkyl, or a pharmaceutically acceptable salt thereof.

The invention relates first and foremost to pharmaceutical compositions which comprise, as compound of formula I, the disodium salt of 3-amino-1-hydroxypropane-1,1-diphosphonate-hereinafter called disodium pamidronate-and, as macrocyclic polyether, (+)-1,4,7,10,13,16-hexaoxacyclooctadecane-2,3,11,12-tetracarboxylic acid or a pharmaceutically acceptable salt thereof.

The invention also relates to a process for the preparation of the novel pharmaceutical compositions, which process can be carried out by known methods and comprises processing a pharmaceutically useful methanediphosphonic acid derivative and a macrocyclic polyether of formula II with conventional pharmaceutically acceptable excipients and adjuvants.

The invention further relates to a process for increasing the peroral resorption of pharmaceutically useful methanediphosphonic acid derivatives, which process comprises blending a pharmaceutically useful methanediphosphonic acid derivative, together with a macrocyclic polyether of formula II as defined above, into a pharmaceutical composition.

The invention relates most particularly to the pharmaceutical compositions described in the Examples and to the preparation thereof.

Depending on the choice of starting materials and procedures, the pharmaceutically useful methanediphosphonic acid derivatives can be obtained in the form of a possible isomer or of a mixture of isomers, typically as optical isomers such as enantiomers or diastereoisomers or geometric isomers, typically cis-trans isomers. The optical isomers are obtained in the form of the pure antipodes and/or as racemates.

The pharmaceutically useful methanediphosphonic acid derivatives can also be used in the form of their hydrates or include other solvents used for their crystallisation. The pharmaceutical compositions of this invention for peroral administration typically contain the pharmaceutically useful methanediphosphonic acid derivatives in a pharmacologically active amount. The daily dose of active drug will depend on the age and individual condition of the patient and also on the mode of application.

It is expected that an approximate daily dose of 0.2 to 200 mg/kg, preferably of 1 to 50 mg/kg, will be administered to a warm blooded animal having a body weight of 75 g in one dose or in a number of partial doses.

Suitable dosage forms are preferably capsules, typically hard or soft gelatin capsules, sachets, coated tablets, typically enteric-coated tablets, or dragée cores, and also solutions.

Formulations in single unit dose form contain preferably from about 1% to about 90%, and formulations not in single unit dose form contain preferably from about 0.1% to about 20%, of the mixture of drug/macrocyclic polyether. Unit dose forms such as capsules, tablets or dragées contain e.g. from about 1 mg to about 500 mg of the mixture of drug/macrocyclic polyether.

The pharmaceutical compositions of this invention are prepared in a manner known per se, typically by conventional mixing, granulating, confectioning, dissolving or lyophilising methods. Pharmaceutical compositions for peroral administration can conveniently be obtained by combining the active drug and the macrocyclic polyether with one or more than one solid carrier and granulating a mixture so obtained. The mixture or granulate can, if desired, be provided with one or more than one coat to give pellets. The mixture, granulate or pellets can, if desired, be processed to tablets or dragées cores by addition of further adjuvants.

Suitable carriers are preferably fillers such as sugars, typically lactose, saccharose, mannitol or sorbitol, and/or cellulose preparations, and also binders such as starches, typically maize, corn, rice or potato starch, methyl cellulose, hydroxypropyl methyl cellulose, sodium carboxymethyl cellulose and/or polyvinyl pyrrolidone, and/or, if desired, disintegrators such as the above mentioned starches, also carboxymethyl starch, crosslinked polyvinyl pyrrolidone, alginic acid or a salt thereof such as sodium alginate.

Additional adjuvants are in particular glidants and lubricants such as silica, talcum, stearic acid and/or polyethylene glycol, or derivatives thereof.

Sachets are small packs, typically of polyethylene, laminated paper or aluminium, which contain the granulate or also pellets direct. Upon opening, the granulate or pellets are either ingested direct or mixed with water before ingestion.

Dragées cores can be provided with non-enteric or enteric coatings using, inter alia, concentrated sugar solutions which may contain gum arabic, talcum, polyvinyl pyrrolidone, polyethylene glycol and/or titanium dioxide, shellac solutions in suitable organic solvents or mixtures of solvents or, for the preparation of enteric coatings, solutions of suitable cellulose preparations such as acetyl cellulose phthalate or hydroxypropyl methyl cellulose phthalate. Dyes or pigments can be added to the tablets or dragées coatings, conveniently to identify or indicate different doses of active drug.

Preferred pharmaceutical compositions for peroral administration are dry-filled capsules of gelatin and soft-sealed capsules consisting of gelatin, a plasticiser such as glycerol or sorbitol. The dry-filled capsules can contain the active drug/macrocyclic polyether in the form of a granulate, conveniently in admixture with fillers such as corn starch, binders and/or glidants such as talcum, and with or without stabilisers. In soft capsules the mixture of active drug/macrocyclic polyether is preferably dissolved or suspended in a suitable liquid adjuvant, typically a fatty oil, paraffin oil or liquid polyethylene glycol, to which a stabiliser may be added.

The invention is illustrated by the following Example.

EXAMPLE 1

Gelatin capsules containing 0.25 g of a mixture of active drug/macrocyclic polyether may be typically be prepared as follows:

| Composition (for 5000 capsules) | |
|---|---|
| disodium pamidronate pentahydrate ( 250 g of anhydrous disodium pamidronate) | 328.83 g |
| (+)-18-crown-6-tetracarboxylic acid | 1000 g |
| corn starch | 120 g |
| stearic acid | 80 g |
| lactose | 20 g |

The powdered substances are passed through a sieve having a mesh size of 0.6 mm and mixed. Gelatin capsules are each filled with 0.31 g of the mixture on a capsule filling machine.

What is claimed is:

1. A pharmaceutical composition comprising
(1) at least one pharmaceutically useful methanediphosphonic acid derivative of formula I

wherein $R_1$ is hydrogen or hydroxy; $R_2$ is —A—$R_3$, wherein A is lower alkylene; and $R_3$ is hydrogen;
unsubstituted amino or amino which is mono- or disubstituted by lower alkyl,
or a pharmaceutically acceptable salt thereof;
(2) at least one macrocyclic polyether of formula II

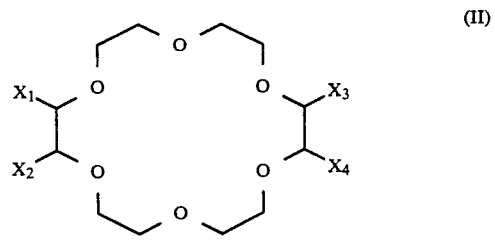

wherein $X_1$–$X_4$ are each independently of the other carboxy, carbamoyl or N-mono- or N,N-disubstituted carbamoyl, or a pharmaceutically acceptable salt thereof; and optionally
(3) pharmaceutically acceptable adjuvants.

2. A pharmaceutical composition according to claim 1 comprising a pharmaceutically useful methanediphosphonic acid of formula I, wherein $R_1$ is hydroxy and $R_2$ is —A—$R_3$, wherein A is $C_1$-$C_7$alkylene and $R_3$ is amino, di-$C_1$-$C_5$alkylamino, or a pharmaceutically acceptable salt thereof.

3. A pharmaceutical composition according to claim 1 comprising a pharmaceutically useful methanediphosphonic acid of formula I, wherein $R_1$ is hydroxy; $R_2$ is —A—$R_3$, wherein A is methylene, ethylene, propylene or pentylene; and $R_3$ is amino, dimethylamino, N-methyl-N-n-propylamino, N-methyl-N-n-pentylamino; or a pharmaceutically acceptable salt thereof.

4. A pharmaceutical composition according to claim 1 comprising as pharmaceutically active methanediphosphonic acid derivative a compound of formula Ia

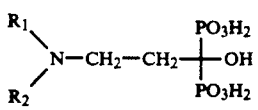

wherein $R_1$ and $R_2$ are each independently of the other hydrogen or $C_1-C_3$alkyl, or a pharmaceutically acceptable salt thereof.

5. A pharmaceutical composition according to claim 1 comprising as methanediphosphonic acid derivative 3-amino-1-hydroxypropane-1,1-diphosphonic acid or a pharmaceutically acceptable salt thereof.

6. A pharmaceutical composition according to claim 5 comprising as methanediphosphonic acid derivative the disodium salt of 3-amino-1-hydroxypropane-1,1-diphosphonic acid.

7. A pharmaceutical composition according to claim 1 comprising as methanediphosphonic acid derivative 3-(N,N-dimethylamino)-1-hydroxypropane-1,1-diphosphonic acid or a pharmaceutically acceptable salt thereof.

8. A pharmaceutical composition according to claim 1 comprising as methanediphosphonic acid derivative 3-(N-methyl-N-n-propylamino)-1-hydroxypropane-1,1-diphosphonic acid or a pharmaceutically acceptable salt thereof.

9. A pharmaceutical composition according to claim 1 comprising a pharmaceutically active methanediphosphonic acid selected from
4-amino-1-hydroxybutane-1,1-diphosphonic acid and
3-(N-methyl-N-n-pentylamino)-1-hydroxypropane-1,1-diphosphonic acid or pharmaceutically acceptable salts thereof.

10. A pharmaceutical composition according to claim 1 comprising as macrocyclic polyether of formula II a compound of formula IIa

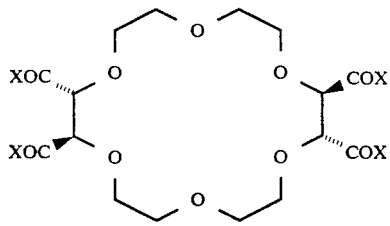

wherein the substituents X are identical and are hydroxy, or a pharmaceutically acceptable salt thereof.

11. A pharmaceutical composition according to claim 6 comprising the disodium salt of 3-amino-1-hydroxypropane1,1-diphosphonic acid and (+)-1,4,7,10,13,16-hexaoxacyclooctadecane-2,3,11,12-tetracarboxylic acid, or a pharmaceutically acceptable salt thereof.

12. A pharmaceutical composition according to claim 1, which contains the pharmaceutically useful methanediphosphonic acid derivative(s) and the macrocyclic polyether(s) in a ratio of 1:1 to 1:16.

13. A pharmaceutical composition according to claim 1, which contains the pharmaceutically useful methanediphosphonic acid derivative(s) and the macrocyclic polyether(s) in a ratio of 1:1 to 1:8.

14. A pharmaceutical composition according to claim 1, which contains the pharmaceutically useful methanediphosphonic acid derivative(s) and the macrocyclic polyether(s) in a ratio of 1:2 to 1:6.

15. A method for the treatment of hypercalcaemia or osteolytic bone metastases in a mammal comprising administering to said mammal a therapeutically effective amount of a pharmaceutical composition comprising (1) at least one pharmaceutically useful methanediphosphonic acid derivative of formula I

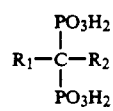

wherein $R_1$ is hydrogen or hydroxy; $R_2$ is —A—$R_3$, wherein A is lower alkylene; and $R_3$ is
hydrogen;
unsubstituted amino or amino which is mono- or disubstituted by lower alkyl,
or a pharmaceutically acceptable salt thereof; (2) at least one macrocyclic polyether of formula II

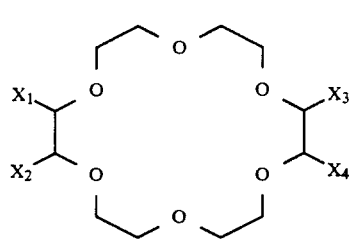

wherein $X_1-X_4$ are each independently of the other carboxy, carbamoyl or N-mono- or N,N-disubstituted carbamoyl, or a pharmaceutically acceptable salt thereof; and optionally (3) pharmaceutically acceptable adjuvants.

* * * * *